US007638519B2

(12) United States Patent
Bush et al.

(10) Patent No.: US 7,638,519 B2
(45) Date of Patent: Dec. 29, 2009

(54) COMPOUNDS, PHARMACEUTICAL COMPOSITIONS, AND METHODS FOR THE TREATMENT OF CARDIOVASCULAR DISEASE

(75) Inventors: Erik Bush, Erie, CO (US); Larry Melvin, Longmont, CO (US)

(73) Assignee: Myogen, Inc., Westminster, CO (US)

( * ) Notice: Subject to any disclaimer, the term of this patent is extended or adjusted under 35 U.S.C. 154(b) by 438 days.

(21) Appl. No.: 11/018,383

(22) Filed: Dec. 21, 2004

(65) Prior Publication Data

US 2005/0288331 A1    Dec. 29, 2005

Related U.S. Application Data

(60) Provisional application No. 60/531,854, filed on Dec. 23, 2003.

(51) Int. Cl.
  *C07D 215/38*   (2006.01)
  *A61K 38/45*    (2006.01)
(52) U.S. Cl. .................................. 514/256; 546/114
(58) Field of Classification Search ................ 546/114; 514/256
   See application file for complete search history.

(56) References Cited

U.S. PATENT DOCUMENTS

| 5,093,493 | A | 3/1992 | Thompson et al. | ........... 544/126 |
| 6,974,870 | B2* | 12/2005 | Cywin et al. | ................. 546/114 |
| 7,119,102 | B2* | 10/2006 | Chen et al. | ................... 514/301 |

FOREIGN PATENT DOCUMENTS

| WO | WO 2006/103511 | 10/2006 |
| WO | WO 2006/122944 | 11/2006 |
| WO | WO 2006/125812 | 11/2006 |

OTHER PUBLICATIONS

Bush et al., "A small molecular activator of cardiac hypertrophy uncovered in a chemical screen for modifiers of the calcineurin signaling pathway," *Proc. Natl. Acad. Sci. USA*, 101:2870-2875, 2004.
Kireev et al., "Molecular modeling and quantitative structure-activity studies of anti-HIV-1 2-heteroarylquinoline-4-amines," *Eur. J. Med. Chem.*, 30:395-402.
Ming et al., "Heterocondensed Pyridines by Cycloaddition-Extrusion Sequence of Bi- and Tricyclic 1,3-Oxaziones with N,N-Diethyl-1-propynylamine," *Chem. Ber.*, 120:1427-1431, 1987.
Pinard et al., "4-Aminoquinolines as a Novel Class of NR1/2B Subtype Selective NMDA Receptor Antagonists," *Bioorganic & Med. Chem. Lett.*, 12:2615-2619, 2002.
Strekowski et al., "Synthesis and Quantitative Structure-Activity Relationship Analysis of 2-(Aryl or Heteroaryl)quinolin-4-amines, a New Class of Anti-HIV-1 Agents," *J. Med. Chem.*, 34:1739-1746, 1991.
Valenti et al., "Acetylcholinesterase inhibition by tacrine analogues," *Bioorg. & Med. Chem. Lett.*, 7:2599-2602, 1997.

Al-Omran, "Aynthesis and biological effects of new derivatives of benzotriazole as antimicrobial and antifungal agents," *J. Heterocyclic Chem.*, 39:877-883, 2002.
Casnati et al., "Some synthetic applications of the reaction of reductive opening of the isoxazole ring," *Tet. Lett.*, 233-238, 1966.
Gewald et al., "Synthesen von 4-amino-thieno[2,3—b]pyridinen," *Monatshefte fur Chemie*, 110:1189-1196, 1979.
Kandeel, "Nitriles in heterocyclic synthesis: a novel synthesis of some thieno[2,3-d]primidine and thieno[2,3-b]pridine derivatives," *Heteroatom Chemistry*, 7:29-33, 1966.
Mohareb et al., "Synthetic potentialities of thiophene systems in heterocyclic synthesis: a novel synthesis of thieno[2,3-b]pyridine derivatives," *Phosphorous, Sulfur and Silicon and the Related Elements*, 155:215-233, 1999.
Strekowski et al., "A facile synthesis of 2-aryl- and 2-heteroaryl-substituted 4- aminoquinolines," *Heterocycles*, 29:539-545, 1989.
Strekowski et al., "Synthesis of 2,2,4-trisubstituted-1,2-dihydroquinazolines," *J. Heterocyclic Chem.*, 26:923-928, 1989.
Strekowski et al., "Synthesis of bis(2-arylquinolin-4-yl)amines by lithium bis(trimenthylsilyl)amide-mediated cyclization of ketimines derived from 2-(trifluoromethy)anilines and aryl methyl ketones," *J. Org. Chem.*, 62:4193-4196, 1997.
Thomsen and Torssell, "Synthesis of simple quinoline alkaloids. A novel quinazoline synthesis," *Acta Chimica Scandinavica, Series B: Organic Chemistry and Biochemistry*, B42:309-313, 1988.
Young et al., *Handbook of Applied Therapeutics*, 7.1-7.12 and 9.1-9.10, 1989.
Fitzgerald et al., "Possible role of valvular serotonin 5-HT2B receptors in the cardiopathy associated with fenfluramine," *Molecular Pharmacology*, 57:75-81, 2000.
Knowles and Ramage, "Evidence for a role for central 5-HT$_{2B}$ as well as 5-HT$_{2A}$ receptors in cardiovascular regulation in anaesthetized rates," *British Journal of Pharmacology*, 128:530-542, 1999.
Ogawa et al., "Pharmacological profiles of R-96544, the active form of a novel 5-HT$_{2A}$ receptor antagonist R-102444," *European Journal of Pharmacology*, 457:107-114, 2002.
Villalón et al., "Serotonin receptors as cardiovascular targets," *Drug Discov. Today*, 2(7):294-300, 1997.
Office Communication issued in European Application No. EP04815043, dated Feb. 29, 2008.
Frishman et al., "Serotonin and serotonin antagonism in cardiovascular and non-cardiovascular disease," *J. Clin. Pharmacol.*, 35:541-572, 1995.

* cited by examiner

*Primary Examiner*—D. Margaret Seaman
(74) *Attorney, Agent, or Firm*—Fulbright & Jaworski

(57) ABSTRACT

The present invention provides certain compounds, pharmaceutical formulations thereof, and methods for the treatment of conditions mediated by 5-HT2 receptors. These compounds provide for modulation of the signals mediated by 5-HT2 receptors, specifically those receptors in the cardiovascular system. Thus, these compounds may be used alone or in conjunction with other drugs to treat cardiovascular diseases such as, but not limited to, muscle atrophy, cardiac hypertrophy, heart failure, and primary pulmonary hypertension.

4 Claims, No Drawings

COMPOUNDS, PHARMACEUTICAL COMPOSITIONS, AND METHODS FOR THE TREATMENT OF CARDIOVASCULAR DISEASE

This application claims benefit of priority to U.S. Provisional Application Ser. No. 60/531,854, filed Dec. 23, 2003, the entire contents of which are hereby incorporated by reference.

BACKGROUND OF THE INVENTION

I. Field of the Invention

This invention relates to compounds, pharmaceutical compositions and methods for the treatment of cardiovascular diseases that are mediated by serotonin receptors (5-HT2R), and in particular, muscle atrophy, heart failure, cardiac hypertrophy and primary pulmonary hypertension (PPH).

II. Description of Related Art

Muscle atrophy refers to the wasting or loss of muscle tissue resulting from disease or lack of use. The majority of muscle atrophy in the general population results from disuse. People with sedentary jobs and senior citizens with decreased activity can lose muscle tone and develop significant atrophy. This type of atrophy is reversible with vigorous exercise. Bed-ridden people can undergo significant muscle wasting. Astronauts, free of the gravitational pull of Earth, can develop decreased muscle tone and loss of calcium from their bones following just a few days of weightlessness.

Muscle atrophy resulting from disease rather than disuse is generally one of two types, that resulting from damage to the nerves that supply the muscles, and disease of the muscle itself.

Examples of diseases affecting the nerves that control muscles would be poliomyelitis, amyotrophic lateral sclerosis (ALS or Lou Gehrig's disease), and Guillain-Barre syndrome. Examples of diseases affecting primarily the muscles would include muscular dystrophy, myotonia congenita, and myotonic dystrophy as well as other congenital, inflammatory, or metabolic myopathies (muscle diseases).

Common causes of muscle atrophy include: age-related muscle wasting, cerebrovascular accident (stroke), spinal cord injury, peripheral nerve injury (peripheral neuropathy), other injury, prolonged immobilization, osteoarthritis, rheumatoid arthritis, prolonged corticosteroid therapy, diabetes (diabetic neuropathy), burns, poliomyelitis, amyotrophic lateral sclerosis (ALS or Lou Gehrig's disease), Guillain-Barre syndrome, muscular dystrophy, myotonia congenital, myotonic dystrophy, myopathy, cancer-related cachexia, AIDS-related cachexia.

Cardiovascular diseases, and in particular heart failure, are among the leading causes of morbidity and mortality in the world. In the U.S. alone, estimates indicate that 3 million people are currently living with cardiomyopathy and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals (Durand et al., 1995). Although there are other causes of DCM, familial dilated cardiomyopathy has been indicated as representing approximately 20% of "idiopathic" DCM. Approximately half of the DCM cases are idiopathic, with the remainder being associated with known disease processes. For example, serious myocardial damage can result from certain drugs used in cancer chemotherapy (e.g., doxorubicin and daunoribucin), or from chronic alcohol abuse. Peripartum cardiomyopathy is another idiopathic form of DCM, as is disease associated with infectious sequelae. In sum, cardiomyopathies, including DCM, are significant public health problems.

Heart disease and its manifestations, including coronary artery disease, myocardial infarction, congestive heart failure, PPH, and cardiac hypertrophy, clearly present a major health risk in the United States today. The cost to diagnose, treat and support patients suffering from these diseases is well into the billions of dollars. Two particularly severe manifestations of heart disease are myocardial infarction and cardiac hypertrophy. With respect to myocardial infarction, typically an acute thrombocytic coronary occlusion occurs in a coronary artery as a result of atherosclerosis and causes myocardial cell death. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic.

With respect to cardiac hypertrophy, one theory regards this as a disease that resembles aberrant development and, as such, raises the question of whether developmental signals in the heart can contribute to hypertrophic disease. Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to DCM, heart failure, and sudden death. In the United States, approximately half a million individuals are diagnosed with heart failure each year, with a mortality rate approaching 50%.

The causes and effects of cardiac hypertrophy have been extensively documented, but the underlying molecular mechanisms have not been elucidated. Understanding these mechanisms is a major concern in the prevention and treatment of cardiac disease and will be crucial as a therapeutic modality in designing new drugs that specifically target cardiac hypertrophy and cardiac heart failure. As pathologic cardiac hypertrophy typically does not produce any symptoms until the cardiac damage is severe enough to produce heart failure, the symptoms of cardiomyopathy are those associated with heart failure. These symptoms include shortness of breath, fatigue with exertion, the inability to lie flat without becoming short of breath (orthopnea), paroxysmal nocturnal dyspnea, enlarged cardiac dimensions, and/or swelling in the lower legs. Patients also often present with increased blood pressure, extra heart sounds, cardiac murmurs, pulmonary and systemic emboli, chest pain, pulmonary congestion, and palpitations. In addition, DCM causes decreased ejection fractions (i.e., a measure of both intrinsic systolic function and remodeling). The disease is further characterized by ventricular dilation and grossly impaired systolic function due to diminished myocardial contractility, which results in dilated heart failure in many patients. Affected hearts also undergo cell/chamber remodeling as a result of the myocyte/myocardial dysfunction, which contributes to the "DCM phenotype." As the disease progresses so do the symptoms. Patients with DCM also have a greatly increased incidence of life-threatening arrhythmias, including ventricular tachycardia and ventricular fibrillation. In these patients, an episode of syncope (dizziness) is regarded as a harbinger of sudden death.

Diagnosis of dilated cardiomyopathy typically depends upon the demonstration of enlarged heart chambers, particularly enlarged ventricles. Enlargement is commonly observable on chest X-rays, but is more accurately assessed using echocardiograms. DCM is often difficult to distinguish from acute myocarditis, valvular heart disease, coronary artery disease, and hypertensive heart disease. Once the diagnosis of dilated cardiomyopathy is made, every effort is made to identify and treat potentially reversible causes and prevent further heart damage. For example, coronary artery disease and valvular heart disease must be ruled out. Anemia, abnormal tachycardias, nutritional deficiencies, alcoholism, thyroid disease and/or other problems need to be addressed and controlled.

As mentioned above, treatment with pharmacological agents still represents the primary mechanism for reducing or eliminating the manifestations of heart failure. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure.

If diuretics are ineffective, vasodilatory agents may be used; the angiotensin converting (ACE) inhibitors (e.g., enalopril and lisinopril) not only provide symptomatic relief, they also have been reported to decrease mortality (Young et al., 1989). Again, however, the ACE inhibitors are associated with adverse effects that result in their being contraindicated in patients with certain disease states (e.g., renal artery stenosis). Similarly, inotropic agent therapy (i.e., a drug that improves cardiac output by increasing the force of myocardial muscle contraction) is associated with a panoply of adverse reactions, including gastrointestinal problems and central nervous system dysfunction.

Thus, the currently used pharmacological agents have severe shortcomings in particular patient populations. The prognosis for patients with DCM is variable, and depends upon the degree of ventricular dysfunction, with the majority of deaths occurring within five years of diagnosis. Thus, the availability of new, safe and effective agents would undoubtedly benefit patients who either cannot use the pharmacological modalities presently available, or who do not receive adequate relief from those modalities.

SUMMARY OF THE INVENTION

The present invention provides for the active compounds of Formula I, all isomers, positional isomers, diastereomers and enantiomers, and pharmaceutically acceptable salts thereof, and all hydrates, and all crystal polymorphs:

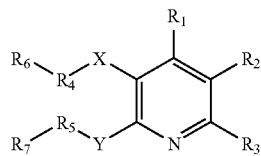

Formula I wherein $R_1$ may be H, OH, $C_{1-6}$-alkyl-O, SH, $C_{1-6}$-alkyl-S, $CH_2$—$NR_8R_9$, and $NR_8R_9$; and $R_2$ may be H, $C_{1-6}$-alkyl, and $C_{1-6}$-cycloalkyl. $R_3$ is phenyl, pyridine, pyrimidine, thiophene, furan, oxazole, isoxazole, thiazole, isothiazole, imidazole, pyrazole and pyrrole, and any of $R_3$ may be optionally substituted by one or more of halogen, $NO_2$, CN, $CF_3$, $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, $SO_2NH$—$C_{0-6}$-alkyl, $SO_2N(C_{1-6}$-alkyl$)_2$, $NHSO_2$—$C_{1-6}$-alkyl, CONH—$C_{0-6}$-alkyl, NHCO—$C_{1-6}$alkyl and COO—$C_{0-6}$-alkyl; $R_4$ and $R_5$ are, independently, H, and both $R_4$ and $R_5$ cannot simultaneously be H, $C_{1-6}$-alkyl, $C_{1-6}$-cycloalkyl; $R_4$ and $R_5$ may also be independently, but not simultaneously, phenyl, pyridine, pyrimidine, thiophene, furan, oxazole, isoxazole, thiazole, isothiazole, imidazole, pyrazole, cyclohexyl, cyclohexenyl, cyclopentyl, cyclopentenyl, tetrahydropyridine, tetrahydrothiophene, and tetrahydrofuran, an aromatic ring or a non-aromatic ring, excluding 3-methyl-2-phenyl-5,6,7,8-tetrahydro-benzo[4,5]thieno[2,3-b]pyridin-4-ylamine and 2-phenyl-quinolin-4-ylamine. In certain embodiments, the aromatic ring may be optionally substituted by one or more of halogen, $NO_2$, CN, $CF_3$, $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, $SO_2NH$—$C_{0-6}$-alkyl, $SO_2N(C_{1-6}$-alkyl$)_2$, $NHSO_2$—$C_{1-6}$-alkyl, CONH—$C_{0-6}$-alkyl, NHCO—$C_{1-6}$-alkyl and COO—$C_{0-6}$-alkyl. In yet further embodiments, the non-aromatic ring may be optionally substituted by one or more of $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, $SO_2NH$—$C_{0-6}$-alkyl, $SO_2N(C_{1-6}$-alkyl$)_2$, $NHSO_2$—$C_{1-6}$-alkyl, CONH—$C_{0-6}$-alkyl, NHCO—$C_{1-6}$-alkyl and COO—$C_{0-6}$-alkyl.

In one embodiment, where $R_1$ is H, then $R_2$ is H, $C_{1-6}$-alkyl, $C_{1-6}$-cycloalkyl, OH, $C_{1-6}$-alkyl-O, SH, $C_{1-6}$-alkyl-S, $CH_2$—$NR_8R_9$ or $NR_8R_9$. In another embodiment where $R_1$ is H and $R_2$ is also H, $C_{1-6}$-alkyl or $C_{1-6}$-cycloalkyl; then $R_4$ is either H, $C_{1-6}$-alkyl, $C_{1-6}$-cycloalkyl, OH, $C_{1-6}$-alkyl-O, SH, $C_{1-6}$-alkyl-S, $CH_2$—$NR_8R_9$ and $NR_8R_9$.

In certain embodiments, X and Y are null, and then $R_4$ and $R_5$ taken together may form a ring selected from phenyl, pyridine, pyrimidine, thiophene, furan, oxazole, isoxazole, thiazole, isothiazole, imidazole, pyrazole, pyrrole, N-methylpyrrole, cyclohexenyl, cyclopentenyl, tetrahydropyridine, dihydrothiophene and dihydrofuran, an aromatic ring, or a non-aromatic ring. In other embodiments, the aromatic ring may be optionally substituted by one or more of halogen, $NO_2$, CN, $CF_3$, $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, $SO_2NH$—$C_0O_6$-alkyl, $SO_2N(C_{1-6}$-alkyl$)_2$, $NHSO_2$—$C_{1-6}$-alkyl, CONH—$C_{0-6}$-alkyl, NHCO—$C_{1-6}$-alkyl and COO—$C_{0-6}$-alkyl. In yet further embodiments the non-aromatic ring may be optionally substituted by one or more of $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, $SO_2NH$—$C_{0-6}$-alkyl, $SO_2N(C_{1-6}$-alkyl$)_2$, $NHSO_2$—$C_{1-6}$-alkyl, CONH—$C_{0-6}$-alkyl, NHCO—$C_{1-6}$-alkyl and COO—$C_{0-6}$-alkyl.

In a variety of embodiments $R_6$ and $R_7$ may be null, H, or are independently but not simultaneously phenyl, pyridine, pyrimidine, thiophene, furan, oxazole, isoxazole, thiazole, isothiazole, imidazole and pyrazole, and $R_6$ or $R_7$ may be optionally substituted by one or more of halogen, $NO_2$, CN, $CF_3$, $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl.

In certain embodiments $R_4$ and $R_5$ form a ring, and $R_6$ and $R_7$ taken together may further form a ring selected from cyclohexyl, cyclohexenyl, cyclopentyl, cyclopentenyl, tetrahydropyridine, hexahydropyridine, dihydrothiophene, tetrahydrothiophene, dihydrofuran and tetrahydrofuran, and each ring may be optionally substituted by one or more of $C_{1-6}$-alkyl, $C_{0-6}$-alkyl-S, $C_{0-6}$-alkyl-O, $C_{0-6}$-alkyl-NH, ($C_{1-6}$-alkyl)$_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl.

In other embodiments $R_8$, $R_9$ and $R_{10}$ are independently H, $C_{1-6}$-alkyl, $C_{1-6}$-cycloalkyl, $C_{1-6}$-alkyl-SO$_2$ and CO—$C_{1-6}$-alkyl; wherein alkyl may be straight or branched chain. In yet further embodiments, X is null, O, S and NR$_{10}$.

In another embodiment, it is envisioned to use the present invention in combination with other therapeutic modalities. Thus, in addition to the therapies described above, one may also provide to the patient more "standard" pharmaceutical cardiac therapies. Examples of other therapies include, without limitation, so-called "beta blockers," anti-hypertensives, cardiotonics, anti-thrombotics, vasodilators, hormone antagonists, iontropes, diuretics, endothelin antagonists, calcium channel blockers, phosphodiesterase inhibitors, ACE inhibitors, angiotensin type 2 antagonists and cytokine blockers/inhibitors, and HDAC inhibitors.

It will be understood that in the discussion of formulations and methods of treatment, references to the compounds of Formula I are meant to also include the pharmaceutically acceptable salts, as well as pharmaceutical compositions comprising these compounds. Also provided are treatments comprising administering to a subject an effective amount of a compound of Formula I, its pharmaceutically acceptable salts, and a pharmaceutically acceptable carrier or formulation.

The term "null" shall mean that the named substitution is absent.

"Cardiovascular disease" includes, but is not limited to, pathological hypertrophy, chronic and acute heart failure.

DETAILED DESCRIPTION OF THE INVENTION

I. The Present Invention

In light of the limitations of the current therapies, and in accordance with the present invention, the inventors herein describe compounds that bind to and modulate the signaling induced by 5-hydroxytryptamine (5-HT2) receptors. These compounds are not only cardioprotective, but also have the ability to modulate non-cardiac muscle cell growth. These receptors are a starting point for a number of important signaling pathways already known to be important in the cellular cascade towards a variety of cardiovascular and muscular conditions. Thus, and in accordance with the present invention, the inventors describe herein compounds, pharmaceutical formulations, and methods of treatment which comprise modulating the expression of and function of 5-HT2 receptors.

II. Compositions

A. Drug Compound

The present invention provides for the active compounds of Formula I:

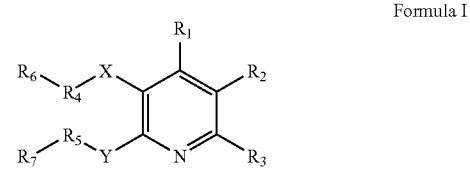

Formula I

Included are all isomers, positional isomers, diastereomers and enantiomers, and pharmaceutically acceptable salts thereof, and all hydrates, and all crystal polymorphs. The substituents of Formula I may be defined as follows: $R_1$ may be H, OH, $C_{1-6}$-alkyl-O, SH, $C_{1-6}$-alkyl-S, CH$_2$—NR$_8$R$_9$, and NR$_8$R$_9$; and $R_2$ may be H, $C_{1-6}$-alkyl, and $C_{1-6}$-cycloalkyl. $R_3$ is phenyl, pyridine, pyrimidine, thiophene, furan, oxazole, isoxazole, thiazole, isothiazole, imidazole, pyrazole and pyrrole, and any of $R_3$ may be optionally substituted by one or more of halogen, NO$_2$, CN, CF$_3$, $C_{1-6}$-alkyl, $C_{0-6}$-alkyl-S, $C_{0-6}$-alkyl-O, $C_{0-6}$-alkyl-NH, ($C_{1-6}$-alkyl)$_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl; $R_4$ and $R_5$ are, independently, H, and both $R_4$ and $R_5$ cannot simultaneously be H, $C_{1-6}$-alkyl, $C_{1-6}$-cycloalkyl; $R_4$ and $R_5$ may also be independently, but not simultaneously, phenyl, pyridine, pyrimidine, thiophene, furan, oxazole, isoxazole, thiazole, isothiazole, imidazole, pyrazole, cyclohexyl, cyclohexenyl, cyclopentyl, cyclopentenyl, tetrahydropyridine, tetrahydrothiophene, and tetrahydrofuran, an aromatic ring or a non-aromatic ring. In certain embodiments, the aromatic ring may be optionally substituted by one or more of halogen, NO$_2$, CN, CF$_3$, $C_{1-6}$-alkyl, $C_{0-6}$-alkyl-S, $C_{0-6}$-alkyl-O, $C_{0-6}$-alkyl-NH, ($C_{1-6}$-alkyl)$_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl. In yet further embodiments, the non-aromatic ring may be optionally substituted by one or more of $C_{1-6}$-alkyl, $C_{0-6}$-alkyl-S, $C_{0-6}$-alkyl-O, $C_{0-6}$-alkyl-NH, ($C_{1-6}$-alkyl)$_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl.

In one embodiment, where $R_1$ is H, then $R_2$ is H, $C_{1-6}$-alkyl, $C_{1-6}$-cycloalkyl, OH, $C_{1-6}$-alkyl-O, SH, $C_{1-6}$-alkyl-S, CH$_2$—NR$_8$R$_9$ or NR$_8$R$_9$. In another embodiment where $R_1$ is H and $R_2$ is also H, $C_{1-6}$-alkyl or $C_{1-6}$-cycloalkyl; then $R_4$ is either H, $C_{1-6}$-alkyl, $C_{1-6}$-cycloalkyl, OH, $C_{1-6}$-alkyl-O, SH, $C_{1-6}$-alkyl-S, CH$_2$—NR$_8$R$_9$ and NR$_8$R$_9$.

In certain embodiments, X and Y are null, and then $R_4$ and $R_5$ taken together may form a ring selected from phenyl, pyridine, pyrimidine, thiophene, furan, oxazole, isoxazole, thiazole, isothiazole, imidazole, pyrazole, pyrrole, N-methylpyrrole, cyclohexenyl, cyclopentenyl, tetrahydropyridine, dihydrothiophene and dihydrofuran, an aromatic ring, or a non-aromatic ring. In other embodiments, the aromatic ring may be optionally substituted by one or more of halogen, NO$_2$, CN, CF$_3$, $C_{1-6}$-alkyl, $C_{0-6}$-alkyl-S, $C_{0-6}$-alkyl-O, $C_{0-6}$-alkyl-NH, ($C_{1-6}$-alkyl)$_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl. In yet further embodiments the non-aromatic ring may be optionally substituted by one or more of $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl.

In a variety of embodiments $R_6$ and $R_7$ may be null, H, or are independently but not simultaneously phenyl, pyridine, pyrimidine, thiophene, furan, oxazole, isoxazole, thiazole, isothiazole, imidazole and pyrazole, and $R_6$ or $R_7$ may be optionally substituted by one or more of halogen, NO$_2$, CN, CF$_3$, $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl.

In certain embodiments $R_4$ and $R_5$ form a ring, and $R_6$ and $R_7$ taken together may further form a ring selected from cyclohexyl, cyclohexenyl, cyclopentyl, cyclopentenyl, tetrahydropyridine, hexahydropyridine, dihydrothiophene, tetrahydrothiophene, dihydrofuran and tetrahydrofuran, and each ring may be optionally substituted by one or more of $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl.

In other embodiments $R_8$, $R_9$ and $R_{10}$ are independently H, $C_{1-6}$-alkyl, $C_{1-6}$-cycloalkyl, $C_{1-6}$-alkyl-SO$_2$ and CO—$C_{1-6}$-alkyl; wherein alkyl may be straight or branched chain. In yet further embodiments, X is null, O, S and NR$_{10}$.

It will be understood that in the discussion of formulations and methods of treatment, references to the compounds of Formula I are meant to also include the pharmaceutically acceptable salts, as well as pharmaceutical compositions comprising these compounds. Also provided are treatments comprising administering to a subject an effective amount of a compound of Formula I, its pharmaceutically acceptable salts, and a pharmaceutically acceptable carrier or formulation.

B. Methods of Preparation and Synthesis

The compounds of the present invention can be prepared according to the following methods or through modifications to these methods by one skilled in the art or in some cases with additions to these methods of other methods readily known to one skilled in the art. The following methods are illustrative examples and do not limit or exclude other methods one skilled in the art may readily utilize or adapt to prepare compounds of this invention. One skilled in the art will also know that many starting materials and intermediates are readily available from various commercial sources or are known through methods reported in the literature or can be obtained through synthetic procedures readily known to one skilled in the art.

Substituted 2-aryl and 2-heteroaryl-4-aminoquinolines can be prepared via the methods of Strekowski et al., *Heterocycles*, 29:539-545, 1989; Strekowski et al., *J. Org. Chem.*, 62:4193-4196, 1997; Strekowski et al., *J. Heterocyclic Chem.*, 26:923-928, 1989; *Phosphorous, Sulfur and Silicon and the Related Elements*, 166:303-314, 2000; *Acta Chimica Scandinavica, Series B: Organic Chemistry and Biochemistry*, B42:309-313, 1988; and *Tet. Lett.*, 233-238, 1966. As a further example of substituted 2-aryl and 2-heteroaryl-4-aminoquinolines the preparation of the following product is illustrated.

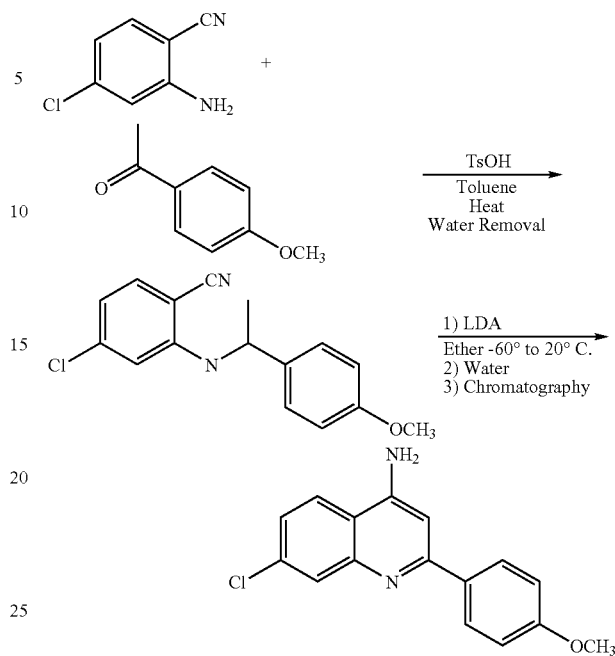

Substituted thieno[2,3-b]pyridines can be prepared via the methods of Thompson et al., U.S. Pat. No. 5,093,493; Gewald et al., Monatshefte fur Chemie, 110:1189-1196, 1979; *Heteroatom Chemistry*, 7:29-33, 1966; *J. Heterocyclic Chem.*, 39:877-883, 2002; *Phosphorous, Sulfur and Silicon and the Related Elements*, 155:215-233, 1999. As a further example of substituted thieno[2,3-b]pyridines the preparation of the following product is illustrated.

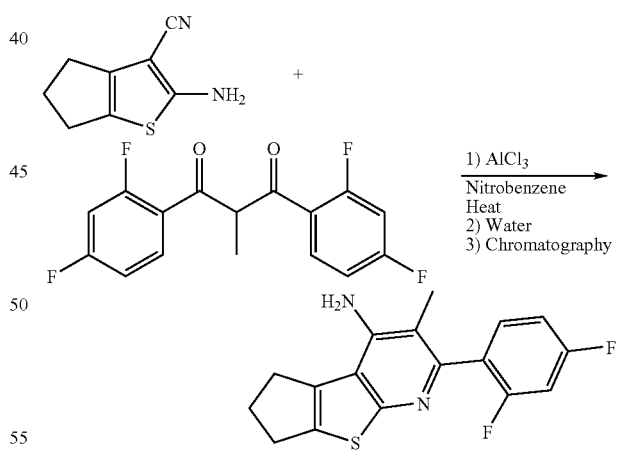

III. Formulations

In specific embodiments of the invention the pharmaceutical formulation will be formulated for delivery via rapid release, other embodiments contemplated include but are not limited to timed release, delayed release, and sustained release. The formulation can be an oral suspension in either the solid or liquid form. In further embodiments, it is contemplated that the formulation can be prepared for delivery via parenteral delivery, or used as a suppository, or be formulated for subcutaneous, intravenous, intramuscular, intraperitoneal, sublingual, transdermal, or nasopharyngeal delivery.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release (hereinafter incorporated by reference).

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures, but liquid at the rectal temperature and will therefore melt in the rectum to release the drug. Such materials are cocoa butter and polyethylene glycols.

For topical use, creams, ointments, jellies, gels, epidermal solutions or suspensions, etc., containing the compound of Formula I are employed. For purposes of this application, topical application shall include mouthwashes and gargles.

The formulation may also be administered as nanoparticles, liposomes, granules, inhalants, nasal solutions, or intravenous admixtures The amount of active ingredient in any formulation may vary to produce a dosage form that will depend on the particular treatment and mode of administration. The previously mentioned formulations are all contemplated for treating patients suffering from cardiovascular disease. It is further understood that specific dosing for a patient will depend upon a variety of factors including age, body weight, general health, sex, diet, time of administration, route of administration, rate of excretion, drug combination and the severity of the particular disease undergoing therapy.

IV. Cardiovascular Diseases

A. Heart Failure and Hypertrophy

Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars. One particularly severe manifestations of heart disease is cardiac hypertrophy. Regarding hypertrophy, one theory regards this as a disease that resembles aberrant development and, as such, raises the question of whether developmental signals in the heart can contribute to hypertrophic disease. Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to DCM, heart failure, and sudden death. In the United States, approximately half a million individuals are diagnosed with heart failure each year, with a mortality rate approaching 50%.

The causes and effects of cardiac hypertrophy have been extensively documented, but the underlying molecular mechanisms have not been fully elucidated. Understanding these mechanisms is a major concern in the prevention and treatment of cardiac disease and will be crucial as a therapeutic modality in designing new drugs that specifically target cardiac hypertrophy and cardiac heart failure. The symptoms of cardiac hypertrophy initially mimic those of heart failure and may include shortness of breath, fatigue with exertion, the inability to lie flat without becoming short of breath (orthopnea), paroxysmal nocturnal dyspnea, enlarged cardiac dimensions, and/or swelling in the lower legs. Patients also often present with increased blood pressure, extra heart sounds, cardiac murmurs, pulmonary and systemic emboli, chest pain, pulmonary congestion, and palpitations. In addition, DCM causes decreased ejection fractions (i.e., a measure of both intrinsic systolic function and remodeling). The disease is further characterized by ventricular dilation and grossly impaired systolic function due to diminished myocardial contractility, which results in dilated heart failure in many patients. Affected hearts also undergo cell/chamber remodeling as a result of the myocyte/myocardial dysfunction, which contributes to the "DCM phenotype." As the disease progresses so do the symptoms. Patients with DCM also have a greatly increased incidence of life-threatening arrhythmias, including ventricular tachycardia and ventricular fibrillation. In these patients, an episode of syncope (dizziness) is regarded as a harbinger of sudden death.

Diagnosis of hypertrophy typically depends upon the demonstration of enlarged heart chambers, particularly enlarged ventricles. Enlargement is commonly observable on chest X-rays, but is more accurately assessed using echocardiograms. DCM is often difficult to distinguish from acute myocarditis, valvular heart disease, coronary artery disease, and hypertensive heart disease. Once the diagnosis of dilated cardiomyopathy is made, every effort is made to identify and treat potentially reversible causes and prevent further heart damage. For example, coronary artery disease and valvular heart disease must be ruled out. Anemia, abnormal tachycardias, nutritional deficiencies, alcoholism, thyroid disease and/or other problems need to be addressed and controlled.

As mentioned above, treatment with pharmacological agents still represents the primary mechanism for reducing or eliminating the manifestations of heart failure. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure.

If diuretics are ineffective, vasodilatory agents may be used; the angiotensin converting (ACE) inhibitors (e.g., enalopril and lisinopril) not only provide symptomatic relief, they also have been reported to decrease mortality (Young et al., 1989). Again, however, the ACE inhibitors are associated with adverse effects that result in their being contraindicated in patients with certain disease states (e.g., renal artery stenosis). Similarly, inotropic agent therapy (i.e., a drug that improves cardiac output by increasing the force of myocardial muscle contraction) is associated with a panoply of adverse reactions, including gastrointestinal problems and central nervous system dysfunction.

Thus, the currently used pharmacological agents have severe shortcomings in particular patient populations. The availability of new, safe and effective agents would undoubtedly benefit patients who either cannot use the pharmacological modalities presently available, or who do not receive adequate relief from those modalities. The prognosis for patients with DCM is variable, and depends upon the degree of ventricular dysfunction, with the majority of deaths occurring within five years of diagnosis.

MEF-2, MCIP, Calcineurin, NF-AT3, and Histone Deactylases (HDACs) are all proteins and genes that have been recently implicated as intimately involved in the development of and progression of heart disease, heart failure, and hypertrophy. Manipulation, modulation, and/or inhibition of any or all of these genes and/or proteins holds great promise in the treatment of heart failure and hypertrophy. These genes are all involved in a variety of cascades that eventually lead to both heart failure and hypertrophy. As such, if there was a way to inhibit these genes or to perhaps prevent the activation of these genes in the first place, that would represent a significant leap in the treatment of cardiac disease. The 5-HT2 subtype of the serotonin receptors are such a potential target, for they are indirectly associated with all of these cascades and thus may represent a therapeutic bottleneck for inhibiting the transcriptional and translational pathways associated with heart failure and hypertrophy.

B. Primary Pulmonary Hypertension

Pulmonary hypertension is a disease characterized by increased pulmonary arterial pressure and pulmonary vascular resistance of the vessels, as well as vascular remodeling which leads to narrowed lumens of the vessels. Pulmonary hypertension can be primary, i.e., of unknown or unidentifiable cause, or can be secondary to a known cause such as hypoxia or congenital heart shunts. The term "primary pulmonary hypertension" (PPH) generally refers to a condition in which there is elevated arterial pressures in the small pulmonary arteries. Pulmonary hypertension generally occurs independently of and is unrelated to systemic hypertension. In vitro studies have concluded that changes in Ca (++) concentrations may be involved in pulmonary tissue damage associated with pulmonary hypertension. (Farruck et al., 1992). A subject having pulmonary hypertension as used herein is a subject having a right ventricular systolic or a pulmonary artery systolic pressure, at rest, of at least 20 mmHg. Pulmonary hypertension is measured using conventional procedures well-known to those of ordinary skill in the art.

Pulmonary hypertension may either be acute or chronic. Acute pulmonary hypertension is often a potentially reversible phenomenon generally attributable to constriction of the smooth muscle of the pulmonary blood vessels, which may be triggered by such conditions as hypoxia (as in high-altitude sickness), acidosis, inflammation, or pulmonary embolism.

Chronic pulmonary hypertension is characterized by major structural changes in the pulmonary vasculature, which result in a decreased cross-sectional area of the pulmonary blood vessels. This may be caused by, for example, chronic hypoxia, thromboembolism, or unknown causes (idiopathic or primary pulmonary hypertension).

Despite the possibility of a varied etiology, cases of primary pulmonary hypertension tend to comprise a recognizable entity. Approximately 65% are female and young adults are most commonly afflicted, though it has occurred in children and patients over 50. Life expectancy from the time of diagnosis is short, about 3 to 5 years, though occasional reports of spontaneous remission and longer survival are to be expected given the nature of the diagnostic process. Generally, however, progress is inexorable via syncope and right heart failure and death is quite often sudden. At least 6% of individuals diagnosed with PPH have a known family history of the disorder. The disease can be classified as being either familial (more than one affected relative has been identified in at least 6% of cases (familial PPH; MIM 178600) or sporadic.

V. Methods of Treating Cardiovascular Diseases

A. Therapeutic Regimens for Heart Failure and Hypertrophy

Heart failure of some forms may curable and these are dealt with by treating the primary disease, such as anemia or thyrotoxicosis. Also curable are forms caused by anatomical problems, such as a heart valve defect. These defects can be surgically corrected. However, for the most common forms of heart failure—those due to damaged heart muscle—no known cure exists. Treating the symptoms of these diseases helps, and some treatments of the disease have been successful. The treatments attempt to improve patients' quality of life and length of survival through lifestyle change and drug therapy. Patients can minimize the effects of heart failure by controlling the risk factors for heart disease, but even with lifestyle changes, most heart failure patients must take medication, many of whom receive two or more drugs.

Several types of drugs have proven useful in the treatment of heart failure: Diuretics help reduce the amount of fluid in the body and are useful for patients with fluid retention and hypertension; and digitalis can be used to increase the force of the heart's contractions, helping to improve circulation. Results of recent studies have placed more emphasis on the use of ACE inhibitors (Manoria and Manoria, 2003). Several large studies have indicated that ACE inhibitors improve survival among heart failure patients and may slow, or perhaps even prevent, the loss of heart pumping activity (for a review see De Feo et al., 2003; DiBianco, 2003).

Patients who cannot take ACE inhibitors may get a nitrate and/or a drug called hydralazine, each of which helps relax tension in blood vessels to improve blood flow (Ahmed, 2003).

Heart failure is almost always life-threatening. When drug therapy and lifestyle changes fail to control its symptoms, a heart transplant may be the only treatment option. However, candidates for transplantation often have to wait months or even years before a suitable donor heart is found. Recent studies indicate that some transplant candidates improve during this waiting period through drug treatment and other therapy, and can be removed from the transplant list (Conte et al., 1998).

Transplant candidates who do not improve sometimes need mechanical pumps, which are attached to the heart. Called left ventricular assist devices (LVADs), the machines take over part or virtually all of the heart's blood-pumping activity. However, current LVADs are not permanent solutions for heart failure but are considered bridges to transplantation.

As a final alternative, there is an experimental surgical procedure for severe heart failure available called cardiomyoplasty (Dumcius et al., 2003). This procedure involves detaching one end of a muscle in the back, wrapping it around the heart, and then suturing the muscle to the heart. An implanted electric stimulator causes the back muscle to contract, pumping blood from the heart. To date, none of these treatments have been shown to cure heart failure, but can at least improve quality of life and extend life for those suffering this disease.

As with heart failure, there are no known cures to hypertrophy. Current medical management of cardiac hypertrophy, in the setting of a cardiovascular disorder includes the use of at least two types of drugs: inhibitors of the rennin-angiotensin system, and β-adrenergic blocking agents (Bristow, 1999). Therapeutic agents to treat pathologic hypertrophy in the setting of heart failure include angiotensin II converting enzyme (ACE) inhibitors and O-adrenergic receptor blocking agents (Eichhorn & Bristow, 1996). Other pharmaceutical agents that have been disclosed for treatment of cardiac hypertrophy include angiotensin II receptor antagonists (U.S. Pat. No. 5,604,251) and neuropeptide Y antagonists (PCT Publication No. WO 98/33791).

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

As can be seen from the discussion above, there is a great need for a successful treatment approach to heart failure and hypertrophy. In one embodiment of the present invention, methods for the treatment of cardiac hypertrophy, PPH, or heart failure utilizing the compounds of Formula I are provided. For the purposes of the present application, treatment comprises reducing one or more of the symptoms of heart failure, PPH, or cardiac hypertrophy, such as reduced exercise capacity, reduced blood ejection volume, increased left ventricular end diastolic pressure, increased pulmonary capillary wedge pressure, reduced cardiac output, cardiac index, increased pulmonary artery pressures, increased left ventricular end systolic and diastolic dimensions, and increased left ventricular wall stress, wall tension and wall thickness, elevated right ventricular systolic pressure, and elevated pulmonary arterial systolic pressures. In addition, use of compunds of Formula I may prevent cardiac hypertrophy, heart failure, or PPH and their associated symptoms from arising.

B. Treatment for PPH

The treatment of pulmonary hypertension by the parenteral administration of certain prostaglandin endoperoxides, such as prostacyclin (also known as flolan), is also known and is the subject of U.S. Pat. No. 4,883,812. Prostacyclin has been administered by inhalation and is used to treat pulmonary hypertension by inhalation (Siobal et al., 2003). A subject at risk of developing pulmonary hypertension may be treated prophylactically to reduce the risk of pulmonary hypertension. A subject with an abnormally elevated risk of pulmonary hypertension is a subject with chronic exposure to hypoxic conditions, a subject with sustained vasoconstriction, a subject with multiple pulmonary emboli, a subject with cardiomegaly and/or a subject with a family history of pulmonary hypertension. These treatments, as with treatments for heart failure and hypertrophy, are not sufficient and thus there is a need to discover methods of treating these diseases that stop the transcriptional and translational cascades that lead to heart damage.

C. Combined Therapy

In another embodiment, it is envisioned to use compounds of Formula I in combination with other therapeutic modalities. Thus, in addition to the therapies described above, one may also provide to the patient more "standard" pharmaceutical cardiac therapies. Examples of other therapies include, without limitation, so-called "beta blockers," anti-hypertensives, cardiotonics, anti-thrombotics, vasodilators, hormone antagonists, inotropes, diuretics, endothelin antagonists, calcium channel blockers, phosphodiesterase inhibitors, ACE inhibitors, angiotensin type 2 antagonists and cytokine blockers/inhibitors, HDAC inhibitors, or TRP channel inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the therapy using compounds of Formula I may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a compound of Formula I, or the other agent will be desired. In this regard, various combinations may be employed. By way of illustration, where the compound of Formula I is "A" and the other agent is "B," the following permutations based on 3 and 4 total administrations are exemplary:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are likewise contemplated.

D. Adjunct Therapeutic Agents

Pharmacological therapeutic agents and methods of administration, dosages, etc., are well known to those of skill in the art (see for example, the "Physicians Desk Reference," Goodman & Gilman's "The Pharmacological Basis of Therapeutics," "Remington's Pharmaceutical Sciences," and "The Merck Index, Thirteenth Edition," incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In addition, it should be noted that any of the following may be used to develop new sets of cardiac therapy target genes as β-blockers were used in the present examples (see below). While it is expected that many of these genes may overlap, new gene targets likely can be developed.

1. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

a. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

b. Resins/Bile Acid Sequesterants

Non-limiting examples of resins/bile acid sequesterants include cholestyramine (cholybar, questran), colestipol (colestid) and polidexide.

c. HMG CoA Reductase Inhibitors

Non-limiting examples of HMG CoA reductase inhibitors include lovastatin (mevacor), pravastatin (pravochol) or simvastatin (zocor).

d. Nicotinic Acid Derivatives

Non-limiting examples of nicotinic acid derivatives include nicotinate, acepimox, niceritrol, nicoclonate, nicomol and oxiniacic acid.

e. Thryroid Hormones and Analogs

Non-limiting examples of thyroid hormones and analogs thereof include etoroxate, thyropropic acid and thyroxine.

f. Miscellaneous Antihyperlipoproteinemics

Non-limiting examples of miscellaneous antihyperlipoproteinemics include acifran, azacosterol, benfluorex, b-benzalbutyramide, carnitine, chondroitin sulfate, clomestrone, detaxtran, dextran sulfate sodium, 5,8,11,14,17-eicosapentaenoic acid, eritadenine, farazabol, meglutol, melinamide, mytatrienediol, ornithine, g-oryzanol, pantethine, pentaerythritol tetraacetate, a-phenylbutyramide, pirozadil, probucol (lorelco), b-sitosterol, sultosilic acid-piperazine salt, tiadenol, triparanol and xenbucin.

2. Antiarteriosclerotics

Non-limiting examples of an antiarteriosclerotic include pyridinol carbamate.

3. Antithrombotic/Fibrinolytic Agents

In certain embodiments, administration of an agent that aids in the removal or prevention of blood clots may be combined with administration of a modulator, particularly in treatment of atherosclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

a. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents

Non-limiting examples of antiplatelet agents include aspirin, a dextran, dipyridamole (persantin), heparin, sulfinpyranone (anturane) and ticlopidine (ticlid).

c. Thrombolytic Agents

Non-limiting examples of thrombolytic agents include tissue plasminogen activator (activase), plasmin, pro-urokinase, urokinase (abbokinase) streptokinase (streptase), anistreplase/APSAC (eminase).

4. Blood Coagulants

In certain embodiments wherein a patient is suffering from a hemhorrage or an increased likelyhood of hemhorraging, an agent that may enhance blood coagulation may be used. Non-limiting examples of a blood coagulation promoting agent include thrombolytic agent antagonists and anticoagulant antagonists.

a. Anticoagulant Antagonists

Non-limiting examples of anticoagulant antagonists include protamine and vitamine K1.

b. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

5. Antiarrhythmic Agents

Non-limiting examples of antiarrhythmic agents include Class I antiarrhythmic agents (sodium channel blockers), Class II antiarrhythmic agents (beta-adrenergic blockers), Class II antiarrhythmic agents (repolarization prolonging drugs), Class IV antiarrhythmic agents (calcium channel blockers) and miscellaneous antiarrhythmic agents.

a. Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocainide (tonocard) and mexiletine (mexitil). Non-limiting examples of Class IC antiarrhythmic agents include encainide (enkaid) and flecainide (tambocor).

b. Beta Blockers

Non-limiting examples of a beta blocker, otherwise known as a b-adrenergic blocker, a b-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

c. Repolarization Prolonging Agents

Non-limiting examples of an agent that prolong repolarization, also known as a Class III antiarrhythmic agent, include amiodarone (cordarone) and sotalol (betapace).

d. Calcium Channel Blockers/Antagonist

Non-limiting examples of a calcium channel blocker, otherwise known as a Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexiline. In certain embodiments a calcium channel blocker comprises a long-acting dihydropyridine (amlodipine) calcium antagonist.

e. Miscellaneous Antiarrhythmic Agents

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyramide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

6. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers

Non-limiting examples of an alpha blocker, also known as an a-adrenergic blocker or an a-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers

In certain embodiments, an antihypertensive agent is both an alpha and beta adrenergic antagonist. Non-limiting examples of an alpha/beta blocker comprise labetalol (normodyne, trandate).

c. Anti-Angiotension II Agents

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-IL type-1 receptor blocker (ARBS), include angiocandesartan, eprosartan, irbesartan, losartan and valsartan.

d. Sympatholytics

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha-1-adrenergic blocker include prazosin (minipress), doxazocin (cardura) and terazosin (hytrin).

e. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(b-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimethylline, trapidil, tricromyl, trimetazidine, troInitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives

Non-limiting examples of miscellaneous antihypertensives include ajmaline, g aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Arylethanolamine Derivatives. Non-limiting examples of arylethanolamine derivatives include amosulalol, bufuralol, dilevalol, labetalol, pronethalol, sotalol and sulfinalol.

Benzothiadiazine Derivatives. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

N-carboxyalkyl(peptide/lactam) Derivatives. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives. Non-limiting examples of dihydropyridine derivatives include amlodipine, felodipine, isradipine, nicardipine, nifedipine, nilvadipine, nisoldipine and nitrendipine.

Guanidine Derivatives. Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines. Non-limiting examples of hydrazines/phthalazines include budralazine, cadralazine, dihydralazine, endralazine, hydracarbazine, hydralazine, pheniprazine, pildralazine and todralazine.

Imidazole Derivatives. Non-limiting examples of imidazole derivatives include clonidine, lofexidine, phentolamine, tiamenidine and tolonidine.

Quanternary Ammonium Compounds. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives. Non-limiting examples of reserpine derivatives include bietaserpine, deserpidine, rescinnamine, reserpine and syrosingopine.

Sulfonamide Derivatives. Non-limiting examples of sulfonamide derivatives include ambuside, clopamide, furosemide, indapamide, quinethazone, tripaamide and xipamide.

7. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

8. Treatment Agents for Congestive Heart Failure

Non-limiting examples of agents for the treatment of congestive heart failure include anti-angiotension II agents, afterload-preload reduction treatment, diuretics and inotropic agents.

a. Afterload-Preload Reduction

In certain embodiments, an animal patient that can not tolerate an angiotension antagonist may be treated with a combination therapy. Such therapy may combine adminstration of hydralazine (apresoline) and isosorbide dinitrate (isordil, sorbitrate).

b. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothizide, hydroflumethizide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetamide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexiline, ticmafen and urea.

c. Inotropic Agents

Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

d. Antianginal Agents

Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

E. Surgical Therapeutic Agents

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

VI. REFERENCES

The following references, to the extent that they provide exemplary procedural or other details supplementary to those set forth herein, are specifically incorporated herein by reference.

U.S. Pat. No. 4,265,874.
U.S. Pat. No. 4,256,108.
U.S. Pat. No. 4,166,452.
U.S. Pat. No. 5,093,493
*Acta Chimica Scandinavica, Series B: Organic Chemistry and Biochemistry*, B42:309-313, 1988.
Durand et al., *Ann. Med.*, 27:311-317, 1995.
Gewald et al., Monatshefte fur Chemie, 110:1189-1196, 1979.
*Heteroatom Chemistry*, 7:29-33, 1966.
*J. Heterocyclic Chem.*, 39:877-883, 2002.
*Phosphorous, Sulfur and Silicon and the Related Elements*, 155:215-233, 1999.
*Phosphorous, Sulfur and Silicon and the Related Elements*, 166:303-314, 2000.
Strekowski et al., *Heterocycles*, 29:539-545, 1989.
Strekowski et al., *J. Heterocyclic Chem.*, 26:923-928, 1989.
Strekowski et al., *J. Org. Chem.*, 62:4193-4196, 1997.
*Tet. Lett.*, 233-238, 1966. Young et al., *Handbook of Applied Therapeutics*, 7.1-7.12 and 9.1-9.10, 1989.

What is claimed is:

1. A compound having the Formula I:

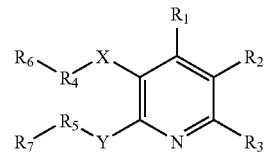

Formula I and pharmaceutically acceptable salts thereof, wherein:

$R_1$ is $NR_8R_9$, wherein $R_8$ and $R_9$ are each H;

$R_2$ is $C_{1-6}$-alkyl, or $C_{1-6}$-cycloalkyl;

$R_3$ is phenyl, pyridine, pyrimidine, thiophene, furan, oxazole, isoxazole, thiazole, isothiazole, imidazole, pyrazole and pyrrole, and any of $R_3$ may be optionally substituted by one or more of halogen, $NO_2$, CN, $CF_3$, $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl;

X and Y are null;

$R_4$ and $R_5$ taken together form a thiophene, which may be optionally substituted by one or more of halogen, $NO_2$, CN, $CF_3$, $C_{1-6}$alkyl, $C_{0-6}$-alkyl-S, $C_{0-6}$-alkyl-O, $C_{0-6}$-alkyl-NH, $C_{1-6}$-alkyl)$_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$-$C_{1-6}$-alkyl, CONH—$C_{0-6}$-alkyl, NHCO—$C_{1-6}$-alkyl and COO—$C_{0-6}$-alkyl;

$R_6$ and $R_7$ are null, H, or are independently but not simultaneously phenyl, pyridine, pyrimidine, thiophene, furan, oxazole, isoxazole, thiazole, isothiazole, imidazole and pyrazole, and any of $R_6$ or $R_7$ may be optionally substituted by one or more of halogen, $NO_2$, CN, $CF_3$, $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, SO$_2$NH-$C_{0-6}$-alkyl, SO$_2$N($C_{1-6}$-alkyl)$_2$, NHSO$_2$—$C_{1-6}$-alkyl, CONH—$C_{0-6}$-alkyl, NHCO-$C_{1-6}$-alkyl and COO-$C_{0-6}$-alkyl;

alkyl may be straight or branched chain;

further comprising all isomers, positional isomers, diastereomers, enantiomers and salts thereof; and excluding 3-methyl-2-phenyl-5,6,7,8-tetrahydro-benzo[4,5]thieno[2,3-b]pyridin-4-ylamine.

2. The compound of claim 1, wherein $R_3$ is phenyl, pyridine, thiophene or furan and any of $R_3$ may be optionally substituted by one or more of halogen, $NO_2$, CN, $CF_3$, $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH-$C_{0-6}$-alkyl, NHCO—$C_{1-6}$-alkyl and COO—$C_{0-6}$-alkyl.

3. The compound of claim 1, wherein $R_6$ and $R_7$ are H.

4. A pharmaceutical composition comprising at least one compound of the formula below or a physiologically acceptable salt thereof in an amount effective to relieve said condition together with at least one physiologically acceptable carrier or exipient:

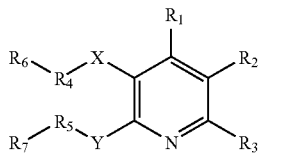

and pharmaceutically acceptable salts thereof, wherein:

$R_1$ is $NR_8R_9$, wherein $R_8$ and $R_9$ are each H;

$R_2$ is $C_{1-6}$-alkyl or $C_{1-6}$-cycloalkyl;

$R_3$ is phenyl, pyridine, pyrimidine, thiophene, furan, oxazole, isoxazole, thiazole, isothiazole, imidazole, pyrazole and pyrrole, and any of $R_3$ may be optionally substituted by one or more of halogen, $NO_2$, CN, $CF_3$, $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$-$C_{1-6}$-alkyl, CONH—$C_{0-6}$-alkyl, NHCO—$C_{1-6}$-alkyl and COO—$C_{0-6}$-alkyl;

X and Y are null;

$R_4$ and $R_5$ taken together form a thiophene ring, which may be optionally substituted by one or more of halogen, $NO_2$, CN, $CF_3$, $C_{1-6}$-alkyl, $C_{0-6}$-alkyl-S, $C_{0-6}$-alkyl-O, $C_{0-6}$-alkyl-NH, $(C_{1-6}$-alkyl$)_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO-$C_{1-6}$-alkyl and COO—$C_{0-6}$-alkyl;

$R_6$ and $R_7$ are null, H, or are independently but not simultaneously phenyl, pyridine, pyrimidine, thiophene, furan, oxazole, isoxazole, thiazole, isothiazole, imidazole and pyrazole, and any of $R_6$ or $R_7$ may be optionally substituted by one or more of halogen, $NO_2$, CN, $CF_3$, $C_{1-6}$-alkyl, $C_{0-6}$-alkyl-S, $C_{0-6}$-alkyl-O, $C_{06}$-alkyl-NH, $(C_{1-6}$-alkyl$)_2$-N, $C_{1-6}$-alkyl-SO, $C_{1-6}$-alkyl-SO$_2$, SO$_2$NH—$C_{0-6}$-alkyl, SO$_2$N($C_{1-6}$-alkyl)$_2$, NHSO$_2$—$C_{1-6}$-alkyl, CONH—$C_{0-6}$-alkyl, NHCO—$C_{1-6}$-alkyl and COO—$C_{0-6}$-alkyl;

alkyl may be straight or branched chain;

further comprising all isomers, positional isomers, diastereomers and enantiomers.

* * * * *

UNITED STATES PATENT AND TRADEMARK OFFICE
CERTIFICATE OF CORRECTION

PATENT NO. : 7,638,519 B2 Page 1 of 1
APPLICATION NO. : 11/018383
DATED : December 29, 2009
INVENTOR(S) : Bush et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1018 days.

Signed and Sealed this

Ninth Day of November, 2010

David J. Kappos
*Director of the United States Patent and Trademark Office*